(12) United States Patent
Goldsmith

(10) Patent No.: US 12,708,703 B2
(45) Date of Patent: Aug. 18, 2026

(54) FULLY IMPLANTED APHERETER/DIALYZERS FOR INTRACORPOREAL BLOOD PURIFICATION

(71) Applicant: David S. Goldsmith, Atlanta, GA (US)

(72) Inventor: David S. Goldsmith, Atlanta, GA (US)

( * ) Notice: Subject to any disclaimer, the term of this patent is extended or adjusted under 35 U.S.C. 154(b) by 590 days.

(21) Appl. No.: 18/358,252

(22) Filed: Jul. 25, 2023

(65) Prior Publication Data

US 2024/0058516 A1 Feb. 22, 2024

Related U.S. Application Data

(63) Continuation-in-part of application No. 15/998,002, filed on Jun. 8, 2018, now Pat. No. 11,759,186, which (Continued)

(51) Int. Cl.
*A61M 1/36* (2006.01)

(52) U.S. Cl.
CPC ... *A61M 1/3618* (2014.02); *A61M 2205/0288* (2013.01); *A61M 2205/8206* (2013.01); *A61M 2210/1078* (2013.01)

(58) Field of Classification Search
CPC ........ A61M 1/3618; A61M 2205/0288; A61M 2205/8206; A61M 2210/1078; A61M 2005/14208; A61M 2005/1726; A61M 2039/2426; A61M 2205/0238; A61M 2205/0272; A61M 2205/04; A61M 2205/50; A61M 2210/1025; A61M 2210/1085; A61M 2240/00; A61M 1/1678; A61M 5/142; A61M 5/14276; A61M 5/1723; A61M 1/28; A61M 1/287;
(Continued)

(56) References Cited

U.S. PATENT DOCUMENTS 4,256,225 A 3/1981 Jackson
5,397,354 A * 3/1995 Wilk ...................... A61F 2/022 623/23.65

(Continued)

*Primary Examiner* — Rebecca E Eisenberg
*Assistant Examiner* — Brandon W. Levy
(74) *Attorney, Agent, or Firm* — Meunier Carlin & Curfman LLC

(57) ABSTRACT

A fully implantable intracorporeal blood purifier for patients with impaired, missing, or normal kidneys overwhelmed by a myeloproliferative disorder such as polycythemia vera, essential thrombocythemia, primary myelofibrosis, or chronic myelogenous leukemia. Functioning continuously or intermittently around the clock, the patient is spared the need to visit the clinic as frequently for treatment, and less severe renal dysfunction may allow the intervals between visits to be considerably extended if not eliminated. The intracorporeal blood purifier represents the extractive or negative component in a prosthetic disorder response system of which the positive component detects the need for and releases medication such as tyrosine-kinase inhibitors—imatinib, and interferon alfa-2b, and cooperates with the purifier to accomplish kidney functions not simply extractive, such as releasing hormones, calcitriol, sodium, and potassium into the blood, maintaining electrolyte, acid-base, and fluid balance, and furnishing small molecule amino acids and glucose by directly targeting the gut.

12 Claims, 3 Drawing Sheets

Related U.S. Application Data is a continuation-in-part of application No. 14/121,365, filed on Aug. 25, 2014, now abandoned.

(60) Provisional application No. 61/959,560, filed on Aug. 27, 2013.

(58) Field of Classification Search
CPC .............. A61M 1/3661; A61M 60/104; A61M 60/109; A61M 60/113; A61M 60/117; A61M 60/122; A61N 2/004; A61F 2/042
See application file for complete search history.

(56) References Cited

U.S. PATENT DOCUMENTS

| | | | |
|---|---|---|---|
| 5,558,640 | A | 9/1996 | Pfeiler et al. |
| 5,601,572 | A | 2/1997 | Middleman et al. |
| 6,030,334 | A | 2/2000 | Cox et al. |
| 6,296,630 | B1 | 10/2001 | Altman et al. |
| 6,497,655 | B1 | 12/2002 | Lindberg et al. |
| 6,620,139 | B1 | 9/2003 | Plicchi et al. |
| 11,759,186 | B2 | 9/2023 | Goldsmith |
| 2002/0151760 | A1 | 10/2002 | Paturu |
| 2003/0065294 | A1 | 4/2003 | Pickup et al. |
| 2003/0171738 | A1 | 9/2003 | Konieczynski et al. |
| 2004/0143242 | A1 | 7/2004 | Ludin et al. |
| 2005/0143801 | A1 | 6/2005 | Aboul-Hosn |
| 2005/0149002 | A1 | 7/2005 | Wang |
| 2006/0041182 | A1 | 2/2006 | Forbes et al. |
| 2006/0129228 | A1 | 6/2006 | Golesworthy et al. |
| 2006/0178647 | A1 | 8/2006 | Stats |
| 2007/0240721 | A1 | 10/2007 | Ho et al. |
| 2008/0004692 | A1 | 1/2008 | Henson |
| 2008/0101677 | A1 | 5/2008 | Maschke et al. |
| 2008/0195146 | A1 | 8/2008 | Wardle |
| 2010/0018534 | A1 | 1/2010 | Veliss et al. |
| 2011/0098662 | A1 | 4/2011 | Zinn |
| 2011/0238034 | A1 | 9/2011 | Kalpin et al. |
| 2012/0172800 | A1 | 7/2012 | Dudar et al. |
| 2012/0277774 | A1 | 11/2012 | Guo |
| 2013/0116667 | A1 | 5/2013 | Ricotti et al. |
| 2014/0163664 | A1 | 6/2014 | Goldsmith |
| 2014/0171899 | A1 | 6/2014 | Rosenberg et al. |
| 2015/0005733 | A1 | 1/2015 | Le et al. |
| 2016/0051806 | A1* | 2/2016 | Goldsmith ............... A61N 1/00 604/21 |
| 2017/0165458 | A1 | 6/2017 | Yu |
| 2018/0085513 | A1 | 3/2018 | Cull |
| 2018/0172685 | A1* | 6/2018 | Wegener ............ A61M 1/3496 |

* cited by examiner

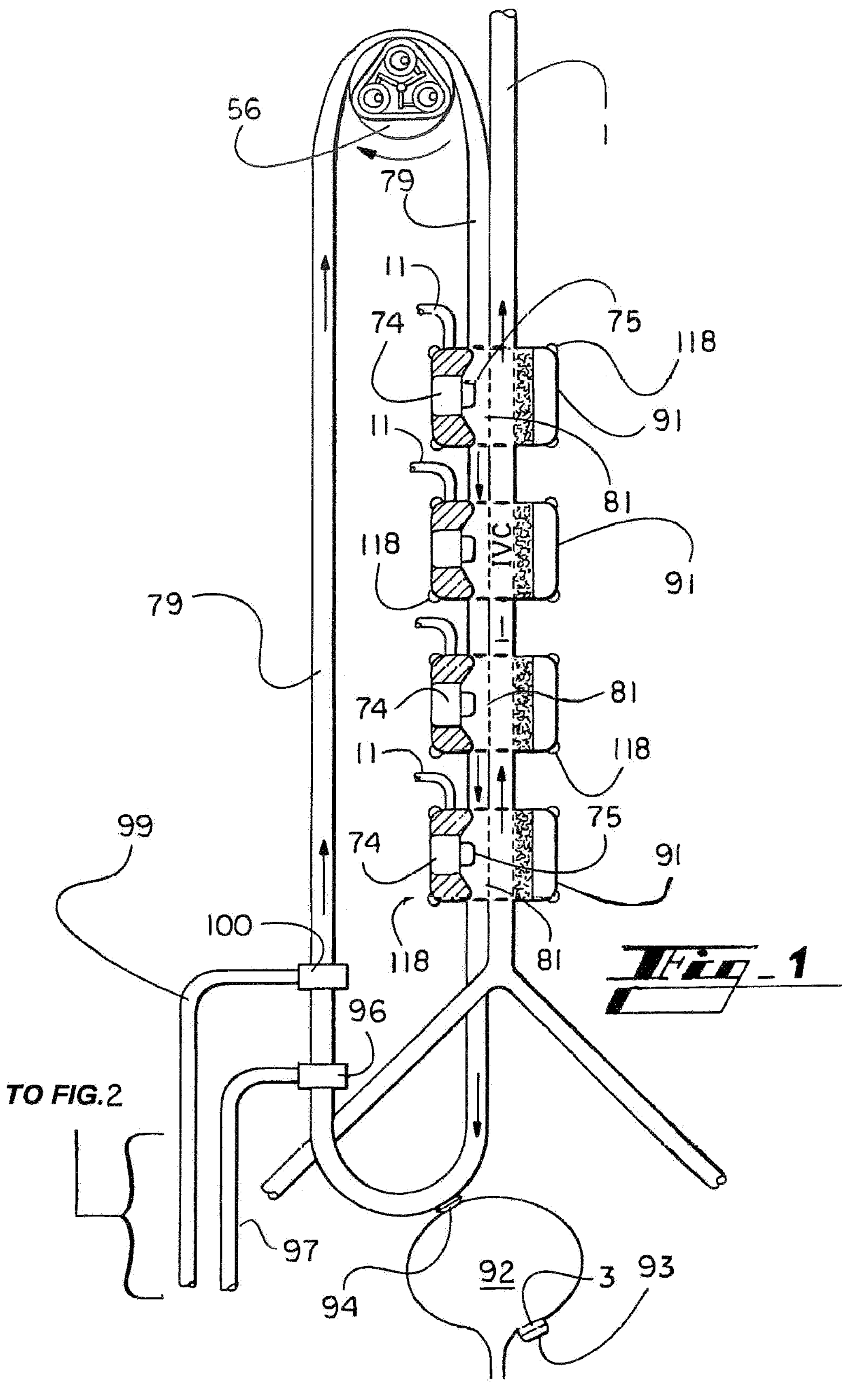
56
1
79
11
74
75
118
91
81
IVC
99
100
96
TO FIG.2
97
94
92
3
93
Fig_1

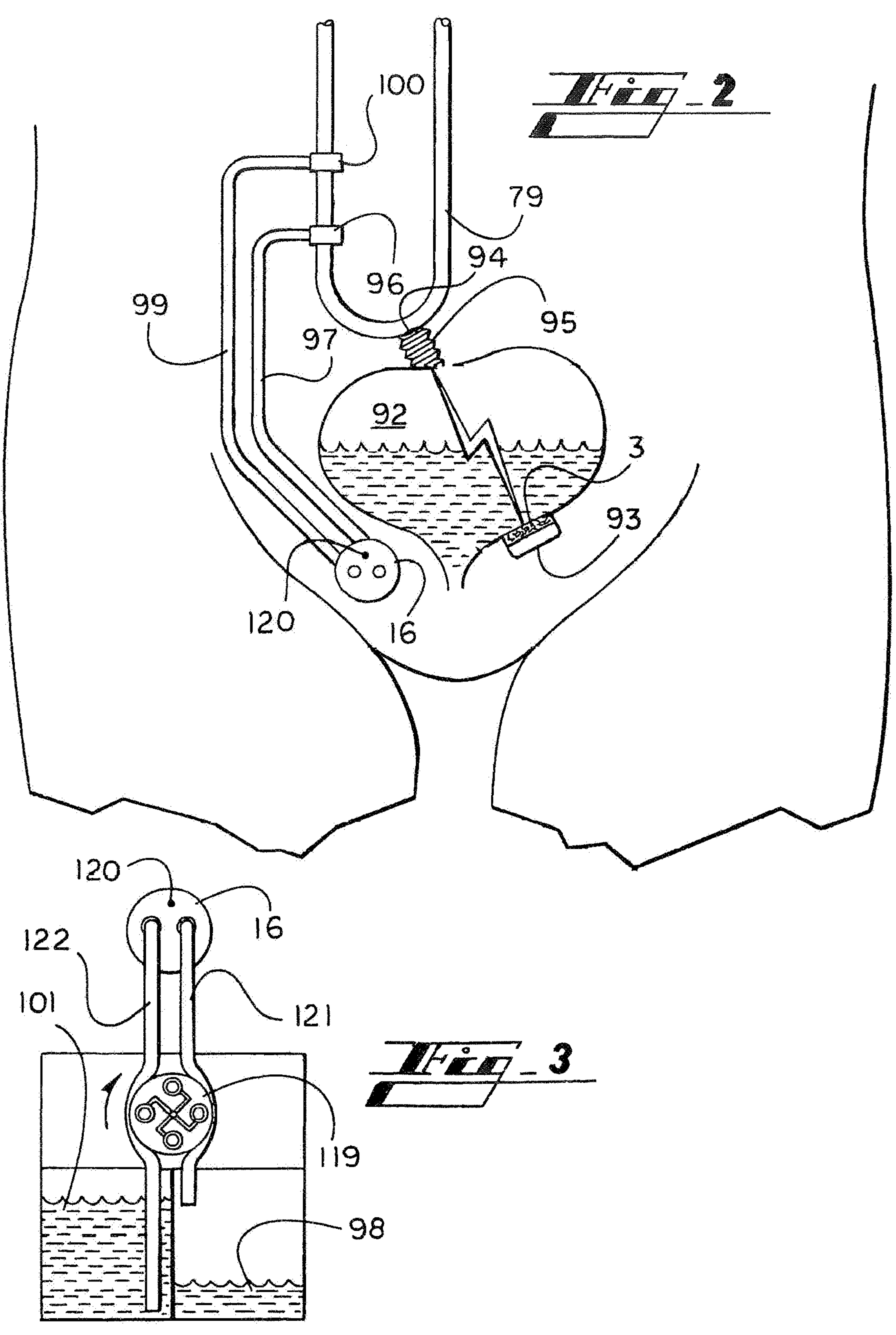
Fig_2
100
79
94
96
95
99
97
92
3
93
120
16
120
16
122
121
101
Fig_3
119
98

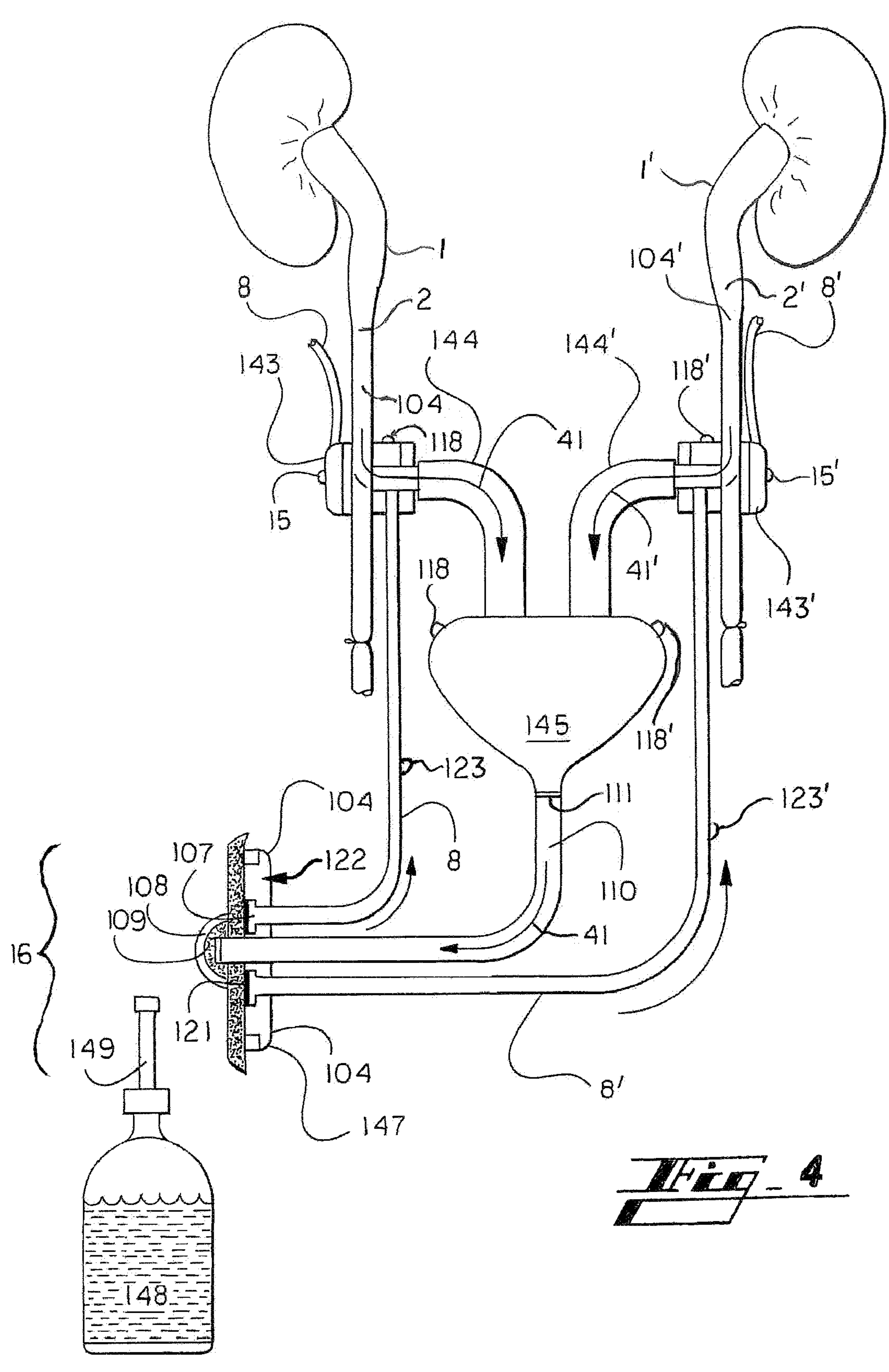
1
1'
2
2'
8
8'
104
104'
143
143'
144
144'
118
118'
41
41'
15
15'
145
123
123'
111
110
122
107
108
109
16
121
149
147
148
Fig_4

FULLY IMPLANTED APHERETER/DIALYZERS FOR INTRACORPOREAL BLOOD PURIFICATION

CROSS REFERENCE TO RELATED APPLICATIONS

This application is a continuation-in-part of U.S. application Ser. No. 15/998,002, entitled Ductus Side-entry Jackets and Prosthetic Disorder Response Systems, filed on Jun. 8, 2018, which is a continuation-in-part of U.S. application Ser. No. 14/121,365, filed Aug. 25, 2014, which claims the benefit of U.S. Provisional Application No. 61/959,560, filed on Aug. 27, 2019, applications which are incorporated herein by reference in their entirety.

1. BACKGROUND OF THE INVENTION a. General

The methods and apparatus to be described are intended for use by hematologists, nephrologists, hepatologists, internists, oncologists, cardiologists and interventional cardiologists, neurologists, dermatologists, general and cardiovascular surgeons, and interventional radiologists to provide patients with a fully implanted, that is, intracorporeal, or inmate, means for extracting pathogenic, toxic, or any other kind of harmful components from their circulatory system. A simple exemplary implanted system for the intracorporeal purification of blood is shown in FIGS. 1-3. Implanted chained magnets can be used for magnetic separation to accomplish apheresis or dialysis where the extractate is drawn into a flush-line and delivered into the urinary bladder for expulsion in the urine.

The development of iron nitride, tetrataenite, and iron-nickel alloys containing phosphorus to accelerate tetrataenite formation magnetics will make possible permanent magnets stronger than those made of neodymium iron boron for incorporation in magnetic separation, or extraction, circuits such as those shown as part number 74 in FIG. 1, and in ferrofluids containing iron-silicon nanoparticles more highly susceptible to magnetic tractive force than superparamagnetic iron oxide nanoparticles currently available to serve as carriers for target analytes in dialysis and apheresis, here circulated through extraction circuit 79 in FIG. 1. The mass and susceptibility of an analyte can be increased by changing the mass of the carrier bonded to it.

Much headway has been made in the development of permanent magnet materials potentially beneficial for medical use (see, for example, Gubert, G., Gubert, P., Sandes, J. M., Bornhorst, J., Alves, L. C., Quines C. B., and Mosca, D. H. 2022. "The Nanotoxicity Assessment of Cube-like Iron Nitride Magnetic Nanoparticles at the Organismal Level of Nematode *Caenorhabditis elegans,*" *Nanotoxicology* 16(4): 472-483; Innovation News Network 2022. "Potential Rare Earth Magnet Replacement Has Been Discovered,' Online at innovationnewsnetwork.com; Ivanov, Y. P., Sarac, B., Ketov, S. V., Jürgen Eckert, A., and Greer, L. 2022. "Direct Formation of Hard-Magnetic Tetrataenite in Bulk Alloy Castings," Online, Advanced Science 10(1):2204315; Wojciechowski, P. and Lewandowski, M. 2022. "Iron Nitride Thin Films: Growth, Structure, and Properties,", Online, [American Chemical Society] Crystal Growth and Design, 22(7):4618-4639; Shibata, M., Kanetaka, H., Furuya, M., Yokota, K., Ogawa, T., and Kawashita, M. 2021. "Cytotoxicity Evaluation of Iron Nitride Nanoparticles for Biomedical Applications," *Journal of Biomedical Materials*

*Research Part A* 109(10):1784-1791; Garcia-Marquez, A., Glaztel, S., Kraupner, A., Kiefer, K., Siemensmeyer, K., and Giordano, C. 2018. "Branch-like Iron Nitride and Carbide Magnetic Fibres Using an Electrospinning Technique," *Chemistry* 24(19):4895-4901).

Extracorporeal blood purification becomes necessary when the response to inadequacies in renal function or to myeloproliferative disease which overwhelms the ability of normal kidneys to dispel arises. Such treatment involves dialysis or apheresis performed during weekly visits to a clinic during which the patient must remain in place for hours. Treatment thus may be necessary to treat an autoimmune disease, a leukemia or lymphoma, or to extract pathogens or atherogenic low density lipoproteins to include lipoprotein(a) from the blood of drug resistant and/or homozygous familial hypercholesterolemic or hypertriglyceridemic patients.

Reducing the amount of low density fat in the blood reduces the risk of forming plaques, of elevated plasma viscosity, and therewith, the shear and oxidative stress caused by blood passing over, possibly rupturing, vulnerable plaques, as well as adversely affecting vascular tone and endothelial function. While reducing the odds favoring plaque formation reduces the risk of coronary heart disease, and reducing the odds of plaque rupture reduces the risk of thromboembolism as the cause of cerebral and myocardial infarctions, reducing an excess of cells in the blood reduces the risk of kidney impairment and occlusion.

In general, all blood related diseases are primarily treated medically and secondarily treated by blood purification when necessary. As described in U.S. application Ser. No. 15/998,002 and in U.S. application Ser. No. 17/689,880, entitled Prosthetic Disorder Response Systems, an implanted prosthetic disorder response system to treat renal or hepatic dysfunction or a myeloproliferative disease incorporates both medicinal and physical extractive means.

With myeloproliferative dyscrasias such as polycythemia vera, a leukemia, lymphoma, or multiple myeloma, which are treated medically and secondarily with physical removal of the cell overload, also dispensed automatically by the implanted automatic response system is medication such as hydroxyurea, ropeginterferon alfa-2b, ruxolitinib, imatinib, or mogamulizumab. A bone marrow or allogeneic stem cell transplant or a splenectomy definitive treatment for a leukemia, medicinal agents include imatinib mesylate and other Bcr-Abl double, or fusion chimeric, gene mutation tyrosine kinase inhibitors.

FIG. 1 shows an intracorporeal blood purifier positioned along the lower part of the inferior vena cava at the level of the fifth lumbar vertebra where it bifurcates into the right and left common iliac veins. The magnet jackets clamping the inferior vena cava to the dialysate, or apherisate, circuit are shown as larger in the drawing figure than these actually are, so that several more magnet jackets could be added continuing to move up the vena cava. Such a blood purification circuit can be designed to target one or more analytes for extraction simultaneously.

For example, the extraction and transit windows 81 through which the magnets draw targeted superparamagnetic, usually iron oxide nanoparticulate carrier-bonded analytes from the blood, can be same or different diffusion type or semipermeable membranes or one-way resilient slit-valves to pass through different analytes or solutes. Successive extraction windows and magnets along the circuit can be the same or different, such as permanent magnets or electromagnets. Slightly curved in concentricity to fit flush against the substrate vein, and slightly larger in diameter than the aperture in the side of the vessel with a blood leak prevention surround, or seal, the semipermeable membrane or one-way slit-valve in an extraction and transit window 81 is part of the magnet-jacket, not the aperture cut in the side of the vessel.

Where the analyte or a solute such as a toxin targeted for extraction would be harmful to the liver, an extraction circuit such as that shown in FIG. 1 is positioned along the hepatic portal vein to intercept and eliminate first pass delivery into the liver. Depending upon the specific morbidity or multimorbidity to be treated, this can be the only circuit or can be secondary to a primary circuit on the inferior vena cava as shown in FIG. 1. Interception for the kidneys is along the abdominal aorta, the foam lining of the magnet-jackets allowing the pulse to pass through each jacket without causing injury. The prospect of extraction circuits on the portal vein, abdominal aorta, and the inferior vena cava at the same time is possible, but especially given the availability of medication to cope with blood dyscrasias, should seldom if even prove necessary.

When the condition of the patient indicates that existing monomorbid disease will progress or lead to multimorbid disease, the secondary circuit, which like that primary is best implanted in an open surgical field, is placed ab initio. A monomorbid condition notwithstanding, in myeloproliferative disease where an overload of a type blood cell would overwhelm and occlude the kidneys, for example, a secondary circuit is implanted to increase the absolute volume of the load extracted. Connections to the urinary bladder and the lines for replenishing the dialysate or apherisate in a circuit on the portal vein are the same as for the circuit shown in FIG. 1, care given to routing the tubing, or lines, such as by subcutaneous tunneling, to disallow strangulation of intervening tissue.

As with conventional apheresis, an intracorporeal blood purifier is intended to cooperate with medicinal agents such as antimicrobials, antileukemics, and enzyme counteractants, for example, to critically reduce if not eradicate supernumerary blood cells and toxins, for example, produced by disease through physical removal. Such an extractive device represents the negative component in a fully implanted prosthetic disorder response system as described in U.S. application Ser. Nos. 15/998,002 and 17/689,880.

At the same time, the release of cooperative medicinals and supplements commonly made necessary by kidney dysfunction, to include calcitriol, blood pressure-adjusting drugs and hormones, mineral metabolism, and substances to maintain electrolyte and blood pH balance, for example, represent the positive component in the prosthetic disorder response system as addressed in U.S. application Ser. No. 17/689,880 just mentioned. In this, the sensor-driven system automatically senses and dispenses these substances as necessary. Accordingly, the coordinated action of the blood purifier and disorder response system discharge the function of an artificial kidney where the blood purifier by itself exceeds the ability of a normal kidney to extract supernumerary blood cells, for example, caused by disease.

Generally, a fully implanted automatic prosthetic disorder response system to treat a monomorbid disease such as kidney failure or a leukemia can be administered by a microcontroller. More often, other bodily systems will be involved as to recommend cross morbidity coordinated treatment administered by a master control microprocessor executing a hierarchical control prescription-program written in Forth to achieve optimal overall homeostasis.

Fully implanted, this system coordinates the operation of the intracorporeal blood purifier and the targeted release of medication. Formulation of drugs in highly concentrated form allows multiple small reservoirs positioned subcutaneously in the pectoral region to store these. Unobtrusive body surface ports, druglines and the connection of these to substrate ductus, and means for drug and energy replenishment are described in U.S. Application Ser. Nos. 15/998,002, and 16/873,914, entitled Vascular Valves and Servovalves—and Prosthetic Disorder Response Systems, FIGS. 26A thru 26C and 27A thru 27C.

Administration of the ferrofluid containing the analyte or solute attractant and magnetic superparamagnetic iron or silicon-iron nanoparticulate carrier is according to the state of the art, oral if possible, for release from the gut into the hepatic portal vein, for example, or systemic through infusion through a small body surface port with drugline connecting directly to a ductus side-entry jacket mounted in perivascular relation to the target substrate ductus.

An essential element in any prosthetic disorder response system, a body surface port represents the point of access for introducing drugs and other essential substances such as system maintenance solutions for direct delivery through a drugline and ductus side-entry jacket, side-entry connector, or vascular valve into the deeply situated tubular anatomical structure, or ductus—most often a blood vessel to which the side-entry connection device is connected. Injection and infusion points are generally placed subcutaneously with a tiny tattoo to expedite their exact location. Almost all body surface ports are influent, the effluent exception being a body surface port in a lower position such as shown in FIGS. 2 thru 4 for passing urine which will usually provide subcutaneous inlet entry points as well as the exposed protectively capped opening of the outlet pipe.

Another reason a port may be positioned on the skin is to house small button cell rechargeable batteries, and/or provide one or more tiny lamps to signal the need for manual intervention. Such a lamp is shown as part number 120 in FIGS. 2 and 3 to signal the need to change the dialysate or apherisate. In some extraordinary cases of multimorbid disease, not all of the system components required will be implantable. Then a surface port to allow fluid and electrical connections with a body pack containing the nonimplantable components may require more than one effluent opening. Such a port is shown in FIGS. 27 and 28 of U.S. application Ser. No. 15/998,002, which also shows a combination inlet/outlet port in FIG. 45.

U.S. application Ser. No. 16/873,914 shows a multiple injection port in FIG. 26A and a combination inlet/outlet port in FIG. 26C. All body surface ports enclose any exposed portion with a cap containing an open-cell foam for saturation with a disinfectant whenever removed. Body surface ports are made as small and unobtrusive, and to the extent possible, positioned subcutaneously with any exposed portion located where clothing keeps the port out of view. When present, a self-sealing needle puncture entry membrane is a feature shared with commercially available portacaths and mediports.

For therapy that demands inordinate attention, and for the very young and very old who cannot be relied upon to adhere to a schedule for dialysis or apheresis and have less than ideal custodial care or difficulty in obtaining transportation, the device works around the clock as the negative, or extractive, component in an implanted automatic prosthetic disorder response system in the treatment of a disease such as myeloproliferative or autoimmune. Such a system, addressed in the parent application hereto and in U.S. application Ser. No. 17/689,880 will usually include a positive, or pharmaceutical prescription-discharging function to release drugs and physiological stabilization substances as well.

This divisional application abridged, the hematological and internal medicine implications of fully implanted aphereter/dialyzers for the intracorporeal purification of blood will be found in the parent application Ser. No. 15/998,002. In general, whereas dialysis is used to extract harmful components from the bloodstream which a normal kidney can extract, apheresis is used to extract harmful components which a normal kidney is unable to extract or is only able to extract up to a point and which are intractable to medical treatment.

Capable of performing cytapheresis around the clock, extracting excessive leukocytes, erythrocytes, or platelets in myeloproliferative disease which two normal kidneys cannot clear out, for example, the intracorporeal blood purification device, or implanted blood purifier, to be described is not properly regarded as an implantable artificial kidney but rather as a fully implanted aphereter/dialyzer suitable for reducing, for example, an overproduction of leukocytes in a leukemic with an unimpaired urinary system which system is thereby assisted so that it might remain normal. By the same token, an artificial kidney is expected to perform the nonextractive functions of a normal kidney as well, for which as the negative or extractive component in a prosthetic disorder response system, the implanted blood purifier must cooperate with and depend upon the positive, or substance deficit and automatic replenishment component.

When required, it represents the negative or extractive complement to the positive or targeted medicinal release capability component executed by a prosthetic disorder response system as presented in U.S. application Ser. No. 15/998,002; U.S. Pat. No. 11,013,858, entitled Nonjacketing Side-entry Connectors and Prosthetic Disorder Response Systems; and U.S. Pat. No. 11,389,171, entitled Integrated System for the Infixion and Retrieval of Implants.

The eventual object of such a blood purification device—to substitute for but expand upon normal kidney function as needed in disease—nonextractive functions to include participation in fluid and electrolyte balance, the release of blood pressure regulating hormones and vitamin D, and the generation of erythrocytes are shared in coordination with the positive complement of the disorder response system.

The pathogenic components in blood include those atherogenic (see, for example, Bambauer, R., Bambauer, C., Lehmann, B., Latza, R., and Schiel, R. 2012. "LDL-apheresis: Technical and Clinical Aspects," Online, *Scientific World Journal* (New York, New York) 2012:314283), those autoimmune (see, for example, Altobelli, C., Anastasio, P., Cerrone, A., Signoriello, E., Lus, G., and 5 others 2022. "Therapeutic Plasmapheresis: A Revision of Literature," Online, *Kidney and Blood Pressure Research* (Basel, Switzerland) 48(1):66-78), hyperleukocytotic (see, for example, Zhang, D., Zhu, Y., Jin, Y., Kaweme, N. M., and Dong, Y. 2021. "Leukapheresis and Hyperleukocytosis: Past and Future," Online, *International Journal of General Medicine* (Auckland, New Zealand) 143457-3467; those malignant (see, for example, Bewersdorf, J. P., Gin, S., Tallman, M. S., Zeidan, A. M and Stahl, M. 2020. "Leukapheresis for the Management of Hyperleukocytosis in Acute Myeloid Leukemia—A Systematic Review and Meta-analysis," Online, *Transfusion* (Arlington, Virginia) 60(10):2360-2369; Connelly-Smith, L. S. and Linenberger, M. L. 2020. "Leukocytapheresis for AML [Acute Myeloid Leukemia] Hyperleukocytosis: Failing to Make the Grade," Online, *Transfusion* (Arlington, Virginia) 60(10):2161-2163; Connelly-Smith, L. S. and Linenberger, M. L. 2015. "Therapeutic Apheresis for Patients with Cancer," Online, *Cancer Control* 22(1):60-78; Pineda, A. A. and Winkelmann, R. K. 1981. "Leukapheresis in the Treatment of Sezary Syndrome," *Journal of the American Academy of Dermatology* 5(5):544-549), as well as those microbial, germs.

Numerous ex vivo proofs of concept for the use of magnetism to extract lymphocytes with alemtuzumab from blood appears in the literature; however, nothing there contemplates incorporating such a process into a fully implanted mechanism for use as an intracorporeal blood purifier able to work around the clock (see, for example, Janker, S., Doswald, S., Schimmer, R. R., Schanz, U., Stark, W. J., Schlapfer, M., and Beck-Schimmer, B. 2023. "Targeted Large-volume Lymphocyte Removal Using Magnetic Nanoparticles in Blood Samples of Patients with Chronic Lymphocytic Leukemia: A Proof-of-Concept Study," Online, Online, MDPI [Multidisciplinary Digital Publishing Institute] *International Journal of Molecular Sciences* (Basel, Switzerland) 24(8):7523; Doswald, S., Herzog, A. F, Zeitner, M., Zabel, A., Pregernig, A., and 4 others 2022. "Removal of Circulating Tumor Cells from Blood Samples of Cancer Patients Using Highly Magnetic Nanoparticles: A Translational Research Project," Online, Pharmaceutics 13(7):1397).

However, in the ability to:

1. Instantly respond to real-time adverse events.
2. Apply to the simultaneous removal of any specific molecules, antigens, and/or cells rendered susceptible in any combination, to include kidney and liver dialysis and any solute which can be precipitated for susceptible carrier bonding. In some cases, even the execution of apheresis and dialysis can be simultaneous.
3. The extraction of any type analyte or combination thereof is without the removal of blood or the need to return the blood into the patient.
4. Be integrated into and immediately supported for the release of pharmaceuticals as directly pipe-targeted to the site affected by a fully implanted prosthetic disorder response system.
5. Eliminate the need for numerous visits to the clinic each of which takes hours.
6. Eliminate the need to sit or lie down in one spot for hours.
7. Eliminate the need for a vascular access susceptible to infection, irritation, and hematoma, access instead afforded through a small cap-sealed infection resistant surface port connected to central lines then connected to their respective substrate great vessels by ductus side-entry jackets as described and illustrated in U.S. application Ser. No. 15/998,002.
8. Provide a material reduction in the cost of treatment.
9. Eliminate electrolyte imbalances, hemodynamic instability, hypocalcemia, impaired bone mineralization, hypovolemia, hypotension, allergic reaction, fatigue, nausea, dizziness, paresthesias, loss of erythrocytes and platelets, irritability, reduced urine output, and femoral vein thrombosis,
10. Immediately produce counteractive measures to deal with any adverse side effect as specified in the system prescription-program.

Considering that apheresis and dialysis have always been synonymous with extracorporeal blood purification, intracorporeal rather than extracorporeal treatment through the implantation of a magnetic aphereter/dialyzer constitutes an improvement that is as critical as it is radical. Nevertheless, a balanced view takes into consideration that extracorporeal apheresis is suitable for harvesting normal blood products for use in the same patient following a surgical procedure, for example, or for use in other patients, which capability is unintended for intracorporeal blood purification.

The best repair for kidney failure is a kidney transplant. However, whether pathogens, the toxic products of kidney or liver malfunction, or of a disease such as a leukemia, blood-borne disease factors are able to survive precisely because these are able to elude and/or overwhelm the ability of the native kidneys to remove them. As with an inborn error in metabolism as a congenital physiological defect, the normal body is not prepared to correct or eradicate every factor that would impair if not kill it.

Whether due to an excess of blood cells, or clotting proteins, or a disease that promotes clotting, the hazards posed by thick or sludgy blood are serious and numerous (see, for example, Perez Rogers, A. and Estes, M. 2023. "Hyperviscosity Syndrome," Treasure Island, Florida: StatPearls Publishing Co.; Gertz, M. A. 2018. "Acute Hyperviscosity Syndromes and Management," Online, *Blood* 132 (13):1379-1385; Zarkovic, M. and Kwaan, H. C. 2003. "Correction of Hyperviscosity by Apheresis," *Seminars in Thrombosis and Hemostasis* 29(5):535-542; Wesenberg, R. L., Rumack, C. M., Lubchenco, L. O., Wirth, F. H., McGuinness, G. A., and Tomlinson, A. L. 1977. "Thick Blood Syndrome," *Radiology* 125(1):181-183; Laufman, H., Gobrewski, R., Treger, N.Y., Method, H., and Venturi, C. A. 1950. "The Significance of the Blood Sludge Phenomenon," Online, *Quarterly Bulletin of the Northwestern University Medical School* 24(4):257-266).

Conventional chelation therapy bonds magnetically nonsusceptible toxic metals to include lead, mercury, arsenic, and copper, to ligands called chelating agents, or chelants, that render the resultant molecule susceptible to extraction by the kidneys. Magnetic blood purification extends this concept to any nocuous substance that can be bonded to a superparamagnetic iron oxide nanoparticulate carrier.

One promising approach mentioned here as compatible with coordinated application by a prosthetic disorder response system, is cellular gene therapy that uses chimeric antigen receptors (CARs, artificial, or chimeric T cell receptors, chimeric immunoreceptors), autologous or allogeneic T or natural killer cells which have been genetically modified to target a pathogenic antigen, typically malignant (see, for example, Abbasi, S. Totmaj, M. A., Abbasi, M., Hajaziman, S., Goleij, P., and 4 others 2023. "Chimeric Antigen Receptor T (CAR-T) Cells: Novel Cell Therapy for Hematological Malignancies," Online, *Cancer Medicine* 12(7):7844-7858; Zhang, C., Durer, S., Thandra, K. C., and Kasi, A. 2022. "Chimeric Antigen Receptor T-cell Therapy," Online, Treasure Island, Florida: StatPearls Publishing Co.' Rohit Reddy, S., Llukmani, A., Hashim, A., Haddad, D. R., Patel, D. S., and 3 others 2021. "The Role of Chimeric Antigen Receptor-T Cell Therapy in the Treatment of Hematological Malignancies: Advantages, Trials, and Tribulations, and the Road Ahead," Online, *Cureus* (Palo Alto, California) 13(2): e13552).

Magnetic Intracorporeal Blood Purification by Removal as a Complement to Automatic Drug, Enzyme, Hormone, and Bioactive Substance Supplementation One object of pharmaceutical practice is to supply protective substances to prevent disease which are not made by the body, or substances to promote or assist normal function in eradicating harmful matter. Another approach is to supply substances to counteract the effects of disease-causing and spreading agents which are not normally produced by the body. Pathogens may have evolved precisely to evade the endogenous or normal means for their eradication. The overproduction of erythrocytes in polycythemia vera, leukocytes in the leukemias and lymphomas, and platelets in thrombocytothemia or thrombocytosis, malfunctions of the immune and hematopoietic systems, can overwhelm, infiltrate, and occlude the kidneys, as well as increase the viscosity of the blood.

The treatment of such diseases as chronic lymphocytic leukemia by an implanted automatic disorder response system which can require both positive medicinal support such as the use of chlorambucil, and negative physical extraction of a system that includes both (see, for example, Tamura, Y., Sumiyoshi, R., Yamamoto, T., Hayama, Y., Fugigaki, Y., and 3 others 2021. "Bilateral Nephromegaly Due to Direct Leukemic Cell Invasion in the Initial and Relapse Phases of T-cell Acute Lymphoblastic Leukaemia: A Case Report," Online, *Medicine* (Baltimore, Maryland) 100(51):e28391; Prada Rico, M., Rodriguez-Cuellar, C. I., Arteaga Aya, L. N., Nunez Chates, C. L., Garces Sterling, S. P., and 4 others 2020. "Renal Involvement at Diagnosis of Pediatric Acute Lymphoblastic Leukemia," Online, *Pediatric Reports* (Basel, Switzerland) 12(1):8382; Rose, A., Slone, S., and Padron, E. 2019. "Relapsed Acute Lymphoblastic Leukemia Presenting as Acute Renal Failure," Online, *Case Reports in Nephrology* (New York, New York) 2019:7913027; Wanchoo, R., Bernabe Ramirez, C., Barrierntos, J., and Jhaveri, K. D. 2018. "Renal Involvement in Chronic Lymphocytic Leukemia," Online, *Clinical Kidney Journal* 11(5):670-680; Sherief, L. M., Azab, S. F., Zakaria, M. M., Karmal, M., Elbasset, Aly, A. I., Ali, A., and Alhady, M. A. 2015. "Renal Presentation in Pediatric Acute Leukemia: Report of 2 Cases," Online, *Medicine* (Baltimore, Maryland) 94(37): e1461; Luciano, R. L. an Brewster, U. C. 2014. "Kidney Involvement in Leukemia and Lymphoma," Online, *Advances in Chronic Kidney Disease* 21(1):27-35; Junglee, N. A., Shrikanth, S., and Seale, J. R. 2012. "Rapidly Progressive Renal Failure Due to Chronic Lymphocytic Leukemia—Response to Chlorambucil," Online, *Indian Journal of Nephrology* (Mumbai, India) 22(3):217-220).

Magnetic separation that supplements or substitutes for the ability of normal or impaired kidneys to extract disease factors from the blood is therapeutic in the opposite sense—of removing agents in the blood associated with disease rather than supplying exogenous substances to effect remediation, the latter entrusted to the positive components of the disorder response system. Similarly, such a mechanism can compensate for the ability of a normal or impaired liver to rid the blood of noxious substances where direct physical extraction from the blood has a place.

Unlike the placement of an artificial knee or hip, the solution does not reinstate but rather supplements normal function. The nonstandard term 'aphereter' responds to the inappropriate application to the type of device to be described as an 'apheresis machine.' In that it is intended to be integrated into the body as if it had been the natural product of evolution to deal with pathophysiology the normal body is unable to eradicate, a prosthetic disorder response system might be referred to as 'bionic'.

The ability of such a fully implanted system to automatically and immediately sense the need for and provide an enzyme, for example, missing as the result of an inborn error in metabolism might be referred to as an additive or supplementary function. In contrast, a magnetic aphereter/dialyzer, no less integrable into a prosthetic disorder response system, responds in the opposite way—rather than by furnishing a missing essential or a medicinal counteractant, when included in the system, this component serves a deductive or depletion function in extracting any blood-borne pathogen or toxic product of disease which can be made magnetically susceptible through bonding to a superparamagnetic nanoparticulate carrier.

Succinctly put; a prosthetic disorder response system can provide what is missing and remove what does not belong and can do both at the same time. Whether applied positively or negatively, the response of the system is to sensor feedback, immediate, and targeted. Where medical treatment is unable to disable a pathogen with an antimicrobial or a toxin through conventional chelation therapy, or reverse a disease process such as inflammation with a steroid, for example, the solution may consist of physical removal.

From this standpoint, an intracorporeal blood purification mechanism is the negative complement to the antipodal positive function of a prosthetic disorder response system in monitoring the patient for the need of medicinal. An enzyme supplement is unambiguously positive, and in the sense that it too is released as a supplement in support of normal function, an enzyme inhibitor is also positive notwithstanding its disabling purpose.

Exposure to a Magnetic Field

The oblivious response of exposure to a magnetic field was a property essential for organisms to live on a planet with a magnetic field, and is evident from the harmless effect of magnetic resonance imaging, for example. Reported adversities may relate to injuries caused by the jerking aside of surgical instruments and the apprehension that follows ingestion by a toddler, which could not be less relevant. Magnetic resonance imaging is widely used throughout most of the world, uses intense magnetic fields, and produces few if any reports of adverse reactions to the use of magnetism.

Exerting no harmful effect on living tissue when properly applied, permanent magnets can be used to extract magnetically susceptible molecule-bound analytes from the blood continuously responsive to a sensor-monitored chronic condition with no input of energy. The use of permanent magnets in medical and dental practice is common (see, for example, Craciunescu, I., Ispas, G. M., Ciorita, A., Leostean, C., Illes, E., and Turcu, R. P. 2023. "Novel Magnetic Composite Materials for Dental Structure Restoration Application," Online, MDPI [Multidisciplinary Digital Publishing Institute] *Nanomaterials* (Basel, Switzerland) 13(7):1215). Electromagnets can respond to sensor inputs that signal the need for the extraction of analytes generated episodically on an as-needed basis and can be adjusted automatically in field strength by the control system to increase the depth and rate of extraction, eliminating the need for a diuretic with its adverse side effects.

To treat a combination of chronic and episodic or acute disease, an implanted aphereter/dialyzer can incorporate both type magnets in combination. Electromagnets are energized only when susceptible-carrier bound analytes are to be extracted; otherwise, these do not generate a magnetic field. As concerns permanent magnets, authors hedge by referring to a 'potential' for harmful effects but are unable to specify any that are medically meaningful or not easily avoided.

Misconceived conclusions are usually attributable to a lack of awareness as to an alternative explanation or methodological limitations in the studies cited (see, for example, Driessen, S., Bodewein, L., Dechent, D., Graefrath, D. Schmiedchen, K., and 3 others 2020. "Biological and Health-related Effects of Weak Static Magnetic Fields (</=1 mT [milliTorr]) in Humans and Vertebrates: A Systematic Review," Online, *PLoS* [Public Library of Science] *One* 15(6):e02300308; Yuksel, C., Ankarali, S., and Yuksel, N. A. 2018. "The Use of Neodymium Magnets in Healthcare and Their Effects on Health," Online, *Northern Clinics of Istanbul* (Istanbul, Turkey) 5(3):268-273).

For clarity, the accompanying drawing figures show a simple system. Specifically, only four magnets are shown, these effectively exaggerated in size because only the lower portion of the vena cava is shown, all along the right-hand side of the apherisate, dialysate, and clear water flush circuit, part number 79, where many might have been shown. In the backside (rear, posterior) schematic view of FIG. 1, the internal foam cushion lining each magnet-jacket makes it possible to clamp the other side of the blood purification circuit along the abdominal aorta without injuring the aorta due to the passing systoles.

In fact, the circuit can continue up along the inferior vena cava, and as indicated, can even position magnet-jackets along the abdominal aorta on the left-hand side as shown, allowing the placement of several more magnets of different kinds with different filtration or extraction and transit windows 81 to include resilient slit- and semipermeable membranes as a major analyte selectivity determinant, along with the affinity for a specific analyte of the magnetically susceptible carrier, attractive field strength applied, and the detailed chemistry of the dialysate or apherisate.

Except that the mass of the analyte is a basis for the selective separation of an analyte both through centrifugation sedimentation and a factor in the degree of its magnetic susceptibility, magnetically based dialysis and apheresis are distinct in physics from conventional methods to include those using semipermeable membrane diffusion. That centrifugation and diffusion are unsuitable for implantation may explain why these processes have remained extracorporeal.

The magnetic extraction of selected analytes from the more highly pressurized aorta would, however, necessitate the use of more powerful magnets in magnet jackets smaller in diameter than for use along the much wider vena cava and more highly susceptible target analyte-bonded carriers. Not showing actual depth, portions of the intracorporeal blood purification device shown in the lower part of FIG. 1 are never coursed through skeletal muscle or dense connective tissue (tendons, ligaments) but rather brought abaxially, that is, outward, toward the body surface, to be positioned subcutaneously (subdermally).

Here where the system extracts the analytes to be discarded without returning blood plasma, for example, into the circulatory system, the dialysate or apherisate solution is formulated solely to expedite extraction, such as the use of dextrose to provide an osmotic gradient that expedites fluid removal and allow for the possibility that some, albeit slight, amount of fluid might gain entry into the bloodstream (see, for example, David, S., Russell, L., Castro, P., van de Louw, A., Zafrani, L., and 13 others 2023. "Research Priorities for Therapeutic Plasma Exchange in Critically Ill Patients," Online, *Intensive Care Medicine Experimental* (Heidelberg, Germany) 11(1):26; Cuadrado, E., Broseta, J. J., Rodriguez-Espinosa, D., Montagud-Marrahi, E., Rodas, L., and 4 others 2022. "Tailoring the Dialysate Bicarbonate Eliminates Predialysis Acidosis and Post-dialysis Alkalosis," Online, *Clinical Kidney Journal* 15(10):1946-1951; Locatelli, F., La Milia, V., Violo, L, Del Vecchio, L, and Di Fillippo, S. 2015. "Optimizing Haemodialysate Composition," Online, *Clinical Kidney Journal* 8(5):580-589; Reverberi, R. and Reverberi, L. 2007. "Removal Kinetics of Therapeutic Apheresis," Online, *Blood Transfusion* (Milan, Italy) 5(3):164-174).

That the succession of magnets along circuit 79 might have been shown as alternated between permanent magnets and electromagnets or combinations of these in the same jacket, or alternate sets of neodymium, iron nitride, stacked permanent magnets, or permanent and electromagnets of which the field strength is gradually increased from one magnet or group thereof to the next along the circuit as the apherisate/dialysate is circulated by the peristaltic pump, part number 56, shown at the top is considered obvious. Electromagnets offer the advantage of allowing only certain of these to be energized at a given time. In the drawing figures, peristaltic, or roller pumps are shown as an immediately apprehended representation of pumping function.

For this reason, pump 56 in FIG. 1, used to circulate the dialysate, apherisate, or combination fluid around circuit 79 and pump 119 used to exchange spent for fresh fluid in the extracorporeal assembly shown in FIG. 3 are shown as peristaltic, or roller, in type. In fact, the type of pumps used is not a factor in the invention, so that if peristaltic pumps produce an insuppressible sensation of internal movement or pulsation while in operation, inline continuous flow pumps such as used in ventricular assist devices are to be preferred. A significant benefit of an implanted prosthetic disorder response system, of which an intracorporeal blood purifier can be a component, is that the detection, signaling, and counteracting of a threat to health is reacted to instantly without the awareness of the patient, medically significant incidents communicated to the clinic by medical telemetry.

Prosthetic disorder response systems, transcutaneous energy transfer, and medical telemetry are addressed in the parent application hereto, Ser. No. 15/998,002, U.S. Pat. No. 11,013,858, U.S. application Ser. No. 17/689,880, U.S. Pat. No. 11,389,171, and in U.S. application Ser. No. 16/873,914.

PRACTICAL IMPLEMENTATION

Due to the continuous function of permanent separation magnets in an implanted blood purification mechanism such as that exemplary shown in FIGS. 1 thru 3, which will considerably extend the intervals separating trips to the clinic, the need to provide electromagnets with power and the additional measures required to use these mentioned just below, and the expense this adds, most such systems, certainly those implemented earlier will use less costly permanent magnets of the polymerase chain reaction separation type. Such magnets are capable of generating flux density and field strength to size and weight ratios which fall within the range required.

For implantation, separation permanent magnets are made of neodymium iron boron and/or when these become commercially available at reasonable cost in the sizes required, iron nitride. Pole reversal by rotating one of two permanent magnets so that the two fields are opposed and cancel out is not considered relevant and does not allow variation in the field force as to simulate the function of an electromagnet. Containing toxic material, permanent magnets must be encapsulated within a biocompatible protective coating. To not cause irritation, much less pain, all magnets for implantation, to include tractive, or separation electromagnets, must be made unobtrusive as possible and enclosed within a biocompatible protective leak-proof outer covering, if necessary, padded.

When not posing excessive size, weight, or cost, magnets used in an implanted blood purification mechanism must generate a field strength sufficient to not only extract the target analytes or metabolites but do so without leaving a residue in the inferior vena cava. If allowed to remain within the lumen wall or other target tissue, current superparamagnetic iron oxide nanoparticles for use as drug-carriers may pose a problem of toxicity (see, for example, Wahajuddin and Arora, S. 2012. "Superparamagnetic Iron Oxide Nanoparticles: Magnetic Nanoplatforms as Drug-carriers," *International Journal of Nanomedicine* 7:3445-3471). This matter is dealt with further in the subsection entitled Hybrid Impasse and Extraction-Jackets, of U.S. application Ser. No. 15/998,002.

To allow the magnets included in the blood purification mechanism, which are close to one another, to be reduced in weight, separate magnetic trap jackets that could be positioned up- or downstream in relation to the implanted blood purification mechanism along the inferior vena cava are also addressed in the copending parent application. The use of outlying trap magnets is not considered if either the need therefor has been discounted because, for example, a negligible residue proves nontoxic and unlikely to pose a problem of embolization, or magnetically susceptible carriers which avoid the problem have been developed. If used at all, electromagnets in separation, or tractive, application will have a core of pure iron rather than air. Resistive rather than superconducting, iron provides optimal permeability.

For tractive rather than portative applications, an electromagnet must use alternating current, and for optimal field strength, coils (solenoids, windings) wound with silver wire. The use of a superparamagnetic silicon-iron nanoparticulate as the component to which the target analyte or analytes, whether directly, or indirectly through the aid of an intermediary substance, are bound at the molecular level imparts maximized magnetic susceptibility for extractive separation. If incorporated into the device, electromagnets are energized only on an as needed, usually intermittent, basis, during which the continuous flow of the apherisate or dialysate past these will prevent the buildup of a sensible degree of heat. The advent of magnetic intracorporeal blood purification should prompt the development of numerous such intermediate substances than currently exist.

To supply power to the implanted aphereter/dialyzer best avoids the need to wear a body pack to hold an inverter and rechargeable battery. Miniaturization of the inverter in the form of a padded solar microinverter with power replenishment through miniature transdermal power transmission components positioned in the abdominal cavity and likewise padded would appear least likely to produce an internal sensation of encroachment without the need for a small partial bowel resection, or colectomy. If placement in the chest is chosen, a partial pulmonectomy, or pneumonectomy, will leave the lung to regenerate as it does with a higher density of alveoli within the restricted space.

2. SUMMARY OF THE INVENTION

Described herein are implanted aphereter/dialyzers operable as intracorporeal blood purifiers devised to allow apheresis or dialysis to be carried out on an intermittent or continuous basis automatically and silently around the clock (e.g. continuously or intermittently) without the awareness of the patient. In this way, the implant materially increases the interval between if not eliminates the need for weekly dialysis, for example.

In one aspect, an arrangement of magnets along and about the inferior vena cava in the abdominopelvic cavity is used to extract any one or a number of pathogenic components from the blood rendered susceptible to magnetic traction by having been bound to substances that incorporate superparamagnetic nanoparticles even if these pathogenic components are not susceptible to extraction through normal kidney function. Circulated against the inferior vena cava behind a filtration membrane backed up by magnets, the apherisate or dialysate delivers the extracted matter directly into the urinary bladder.

As a treatment for an isolated or monomorbid disease, the process is administered by an implanted microcontroller executing a prescription-program. In a system designed to treat comorbid or multimorbid disease, the process is overseen by the master control microprocessor of a prosthetic disorder response system in which intracorporeal blood purification represents but one arm of control in a hierarchical control system. The immediacy of treatment and its coordination with concomitant treatment provides significant advantages in terms of quality of life.

3. OBJECTS OF THE INVENTION

1. As the extractive component in a fully implanted prosthetic disorder response system programmed to sustain chemical balance, to function as a kidney capable of extracting any harmful substance from the blood not the product of disease to which a magnetically susceptible carrier can be bound.
2. In myeloproliferative disease, to exceed normal kidney function by extracting supernumerary leukocytes, erythrocytes, or thrombocytes, for example, for expulsion in the urine.
3. As the negative, or deductive toxin and pathogen extractive component in a disorder response system, to function in coordination with the positive, additive, or medicinally releasing component of the system to which is entrusted the maintenance of fluid and electrolyte balance, the release of blood pressure regulating hormones and vitamin D, and the generation of erythrocytes.
4. To eliminate adverse complications of conventional, or extracorporeal blood purification such as electrolyte imbalances, hemodynamic instability, hypocalcemia, impaired bone mineralization, hypovolemia, hypotension, allergic reaction, fatigue, nausea, dizziness, paresthesias, loss of erythrocytes and/or platelets, irritability, reduced urine output, and femoral vein thrombosis.
5. To deliver the harmful extractates into the urinary bladder for disposal through normal voiding.
6. To reduce the number if not eliminate the need for frequent visits to a clinic where the patient must remain stationary for hours during which the process of removing, purifying, and replacing the patient's blood or exchanging the patient's plasma is carried out.
7. To eliminate the need for a surgically created vascular access susceptible to irritation, infection, and hematoma, access instead through a small cap-sealed body surface port devised for ease of sterilization to communicate with deep lying vessels through side-entry jackets for extracorporeal or intracorporeal dialysis and one of which can serve as a permanently available central line.
8. In a monomorbid application, to respond to an implanted microcontroller receiving sensor inputs and applying remedial measures as prescribed by a dedicated prescription-program controlling a relatively simple fully implanted prosthetic disorder response system to include implanted medicinal reservoirs and druglines as described in U.S. application Ser. No. 15/998,002.
9. In a multimorbid application, to respond to an implanted master control microprocessor receiving sensor inputs and concurrently applying remedial measures such as the release of medication from implanted medicinal reservoirs by having access to and controlling an implanted aphereter/dialyzer as one arm of control in a hierarchical control-governed prescription-program which includes and coordinates this treatment to achieve the optimal overall homeostasis across the combination of comorbidities in a fully implanted prosthetic disorder response system as described in U.S. application Ser. No. 15/998,002 and U.S. application Ser. No. 17/689,880.
10. To instantly respond to any change in the status of the patient for which a prescribed response is included in the system prescription-program supported by implanted medicinal reservoirs.
11. To allow the simultaneous extraction of different type pathogenic components from the blood, whether toxins, pathogens, antigens, and/or abnormal cells continuously and simultaneously.
12. To provide a material reduction in the cost of dialysis and/or apheresis.

4. BRIEF DESCRIPTION OF THE DRAWINGS

FIG. 1 is a rear (posterior, backside) schematic view of a chain of apheresis, hemodialysis, or cytapheresis magnetic extraction, or separation, jackets mounted along an apherisate, and/or dialysate, and water flush line circuit applied to the inferior vena cava to extract analytes rendered magnetically susceptible by having been bound to a superparamagnetic carrier or magnetic intermediary for drop-off of the magnetically separated extractate into the native urinary bladder or a prosthetic neobladder 145 under the tractive force of a subcystic magnet 93 toward the bottom of the FIG. 1 and in 2.

FIG. 2 is a rear (posterior, backside) schematic view looking to the anterior surface of the body from a coronal or frontal plane anterior to the spinal column to provide a closer view of the pelvic, or lower portion of the intracorporeal blood purifier in FIG. 1 showing the mechanism for dropping off the magnetically separated extractate into the urinary bladder.

FIG. 3 shows an apherisate or dialysate disposal and replenishment chamber used to replace spent apherisate or dialysate.

FIG. 4 is a schematic anterior view of a bilateral automatic urine collection and voiding prosthesis.

5. DETAILED DESCRIPTION OF THE INVENTION

FIG. 1 depicts four chained magnet jackets as described in copending parent application Ser. No. 15/998,002, incorporated in its entirety by reference herein, entitled Ductus Side-entry Jackets and Prosthetic Disorder Response Systems, used in an implanted cytapheresis or hemodialysis device. Ordinarily magnetic cytapheresis would supplement medicinal treatment by extraction of the supernumerary cells through a one-way resilient slit-valve positioned in extraction and transit windows 81 separating the vessel lumen from the magnet as the separation filter.

Dialysis such as to extract toxins in the blood would use a semipermeable membrane or as assemblage of these. Here where the implanted device is not conveniently accessible, it can compensate for what would otherwise be a shortcoming by allowing the extraction of more than one kind of analyte simultaneously. In connection with FIGS. 13 thru 15 therein, parent application Ser. No. 15/998,002 addresses series of extraction, or separation magnet jackets spaced along a ductus accompanied by a common flush-through line.

In FIG. 1, part number 56 is a peristaltic, or roller, pump used to circulate a dialysate, apherisate, combination fluid, or flush water through liquid circuit 79; part number; 74 is the body of the magnet if permanent such as neodymium, or the winding if an electromagnet; and 75 is the magnet pole. Parts numbered 81 are extraction transit windows which to filter the target analyte intended can consist of a one-way resilient slit-valve for cytapheresis or a membrane comprising bundled diffusion-type semipermeable fibers for hemodialysis, or a comparable type membrane for low density lipoprotein apheresis, for example. In an embodiment meant to extract different type analytes, two options are available, applied separately or in combination. Suture eyelets 118 are available to pass through suture to effect stabilization of the device if and only if necessary. The lumen of the inferior vena cava shown as IVC is indicated as 1.

Also in FIG. 1, parts numbered 91 are the magnetic separation jackets as a whole. The parts marked 11 are druglines that wind around beneath, hence, out of the section plane of FIG. 1 and therefore, out of sight, in order to pass into the foam lining the magnet jacket to allow the directly pipe-targeted delivery of medication through the open cell foam jacket lining so that it will soak through and wet the adventitia to dispel any irritation. At the bottom of FIG. 1, part number 3 is a schematically indicated protective foam layer separating subcystic magnet 93 separated from the undersurface of the urinary bladder 92 by foam pad 3. Positioned thus, provided it does not come into contact with the roof of the bladder, the magnet can project an extension, arm, or probe upward to reduce the distance separating the target analyte from the magnet.

In FIGS. 1 and 2, part number 92 is the urinary bladder, 93 the magnet beneath the bladder used to draw debris passing through extraction window 94 schematically shown as the diffusion membrane or cytapheresis slit-valve in the side of flush-line 79 and a ringed-, or framed-about, window of complementary shape applied to bladder 92. The first is the use of resilient one-way slit-valves for the simultaneous extraction of multiple type analytes. Where selectivity is sought so that only one analyte or certain analytes are extracted, the one-way slit-valves are made in analyte mass-selective targeting degrees of resilience in combination with the field strength of the magnet so that a given magnet is passed or bypassed.

Where more than a specific analyte or combination of these would be extracted against the intention nevertheless, selectivity between or among analytes is obtained through the use of magnetically susceptible carriers or intermediary substances that express an affinity for a certain analyte as opposed to others. Another means for refining separation or analyte selectivity is to incorporate different analyte-specific separation, or filtering, membranes in successive magnets along the circuit. Dialysates, apherisates, plasma replacement fluids, and distilled flush water are entered into and drained from circuit 79 through solenoid-driven pipe flow diversion valves 96 or 100 accessed through mons pubis mounted body surface port 16 shown in FIG. 2.

FIG. 3 shows a separate extracorporeal dialysate or apherisate disposal and replenishment chamber, or exchanger used to replace spent apherisate or dialysate. As would a collection bag, the disposal and replenishment chamber plugs into surface port 16, but unlike a collection bag, the chamber need not be worn constantly. It should, however, be kept within easy reach for use when turbidimetric sensor-driven lamp 120 signals the need to change the fluid by turning on a small lamp on body surface port 16. Only an extracorporeal embodiment is shown in this application.

In FIG. 3, spent dialysate or apherisate is shown as 98 in the fluid reservoir, well, or chamber on the right, with that fresh shown in the fluid reservoir as 101 on the left, the dialysate or apheresis fluid reservoir, actuating peristaltic, or roller type pump 119 used to circulate the dialysate 56 shown as similar to that shown toward the top of FIG. 1. Pump 119 draws in fresh dialysate or apherisate in line 122 which plugs into the socket or receptible of the left of body surface port 16 which in turn connects line 122 in continuous relation to line 99 in the intracorporeal blood purifier.

When its diversion chute is fully extended, solenoid driven diversion valve 100 passes the dialysate or apherisate into circuit 79 which moves the fluid clockwise to empty through solenoid-driven pipe flow diversion valves 96 with its diversion chute fully extended, thence through pipe 97, through right-hand port socket into extracorporeal line 121 for release into right-hand well 98. Actuation of this process is signaled by lamp 120 responsive to a fluid turbidity level sensor (not shown) situated within well 98. While valves could be specified that would switch from the extracorporeal assembly shown in FIG. 2 to the electrically controllable faucet and the drain of a sink to allow the automatic clear flushing of circuit 79 with water, to empty, wash out. and fill chamber fill 101 with water including a disinfectant without automation accomplishes the sterilization of the extracorporeal chamber and circuit 79 without needless expense.

Solenoid-driven pipe flow diversion valves 96 and 100 incorporate accessory channels which allow the release of medication received through druglines connected to drug reservoirs implanted subcutaneously in the chest directly through the valves and into their respective substrate lines. Copending application Ser. No. 16/873,914 provides detailed descriptions and illustrations of these parts. That drugs can be introduced into the fresh fluid in well 101 is considered obvious.

Once the dialysate, apherisate or a combination formulation fluid in extraction circuit 79 collects a threshold accumulation of debris, a light transmissivity or turbidimetric sensor (not shown) signals the monomorbid system microcontroller or multimorbid master control microprocessor of the prosthetic disorder response system to turn on lamp 120 on body surface port 16. The system then waits for the user or a helper to use an ordinary automobile key bob remote keyless lock control to switch the diversion chutes of solenoid-driven pipe flow diversion valves 96 and 100. Switching is from the fully retracted position whereby flow continues to circulate around circuit 79 to fully extended so that flow is from the fresh fluid in chamber 101 in the extracorporeal fluid storage enclosure through circuit 79 and into chamber 98.

The remote keyless entry fob is then used to stop pump 119, allowing the user or a helper to flush the extracorporeal fluid storage enclosure clean. Water containing a biocompatible disinfectant placed in fresh fluid chamber 101, the remote keyless entry fob is used to start pump 119, thus flushing through circuit 79. Pump 119 is then stopped, chamber 101 filled with fresh dialysate, apherisate, or other extractive fluid, and solenoid-driven pipe flow diversion valves 96 and 100 switched to the fully retracted position, thus closing off circuit 79 for continuous circulation.

FIG. 4 shows a prosthetic replacement for the lower urinary tract. More specifically, it is a schematic anterior view of a bilateral automatic urine collection and voiding prosthesis using one-time manually set valves such as those shown in FIGS. 2 and 3 or solenoid-driven valves such as shown in FIGS. 7 and 8 of copending application Ser. No. 16/873,914, for permanent placement in a patient with a missing or defective lower urinary tract, and therefore lacking urge sensation, to divert the effluent into a synthetic or surgically constructed neobladder 145, or directly into a paracorporeal collection bag cinched about a thigh or urinal 148.

FIG. 4 shows a prosthetic replacement for the lower urinary tract. More specifically, it is a schematic anterior view of a bilateral automatic urine collection and voiding prosthesis using one-time manually set valves such as those shown in FIGS. 2 and 3 or solenoid-driven valves such as shown in FIGS. 7 and 8 of copending application Ser. No. 16/873,914 for permanent placement in a patient with a missing or defective lower urinary tract, and therefore lacking urge sensation, to divert the effluent into a synthetic or surgically constructed neobladder 145, or directly into a paracorporeal collection bag cinched about a thigh or urinal 148.

In FIG. 4, part numbers 143 on the left and 143' on the right are the valves that control flow through native ureters 104 on the left and 104' on the right of which the adventitias are 1 and 1' and the lumina 2 and 2' respectively. Urine is diverted by valves 143 and 143' into prosthetic neoureters 144 on the left and 144' on the right into prosthetic neoureter confluence chamber, or neobladder 145. If and only if it is imperative to reduce its mobility, neobladder 145 is stabilized by passing suture through suture eyelets 118 on the left and 118' on the right for attachment to neighboring tissue. Detailed views of the internal structure of manually operated diversion valves, bistable, or either-or of two opposing positions, solenoid-driven diversion valves, and continuously variable diversion servovalves are shown in the copending application Ser. No. 16/873,914.

On the valve-jackets, suture eyelets for passing through suture to stabilize the prosthesis by connection to neighboring tissue if and only if necessary are shown as 118 on the left 118' on the right, additional suture eyelets to allow vectoring to neighboring tissue to either side shown as 15 and 15'. Urine flow directional lines through neoureters 143 and 143' are shown as 41 and 41' respectively, thence through neobladder 145 and out through neobladder 145 outlet pipe 110 for effluence or discharge as 41. Neobladder 145 likewise has suture stabilization eyelets 118 and 118'.

Similarly, if and only if imperative to maintain contact with the body surface and/or to reduce mobility, rear surface backplate, 104 of port 16 is sutured to the integument at positions 122. Backplate 104 of port 16 is cushioned with an open cell foam only if an emollient containing an antimicrobial for example, is to saturate the interface in order to prevent irritation and reduce the risk of infection. Body surface port 16 is of the combination type addressed above which includes an above-skin urine outlet pipe 110 and injection points 107 and 121 which shown here as sutured to the skin are preferably positioned subcutaneously without the need for suture by having the operator make certain that the port is flush fit to the skin.

Whether above or below skin, and because to suture the rear of port 16 through keyhole incisions is difficult, this is easily accomplished by gently pressing port 16 against the skin and using suture loops 123 and 123' to stabilize it by attachment to neighboring tissue. Injection points 107 and 121 empty into drug delivery lines, or druglines 8 and 8' respectively. The distance from injection points 107 and 121 to diversion valves 143 and 143' respectively is not negotiated by using enough medication to run these distances; rather, the prescribed amount of the drug or drugs is injected first and pushed forward with a column of sterile water.

Junction 111 connects the 'neck' of prosthetic neobladder, or neoureter confluence chamber, 145 to outflow or outlet pipe 110 which terminates at the center of body surface port 16, positioned as shown in FIG. 2, on the left side of the mons pubis, with a side view shown in FIG. 4, and a more detailed view provided in FIG. 45 of copending parent application Ser. No. 15/998,002 and in FIGS. 26C and 28 of copending application Ser. No. 16/873,914.

Open cell foam lining 109 of body surface port 16 protective cover cap 108 allows saturation with a disinfectant every time it is removed to connect collection bottle or urinal 148 through connection pipe 149. Bidirectional, body surface port 16 incorporates not only outflow pipe 110 opening but provides injection points 107 to pipe-target medication through left-hand drugline, or sideline, 8 into the accessory channel of left-hand valve 143 and through right-hand drugline 8' and injection point 121 to pipe-target medication through right-hand drugline, or sideline, 8' into the accessory channel of left-hand valve 143'.

As shown in FIG. 4, depending upon the condition to be treated, a port positioned thus can also incorporate a urine outlet pipe 110 for connection to urine collection bag or urinal 148 connection pipe 149. Not intended to harvest blood products or to remove and return blood, cells, platelets, or plasma into a patient, magnetic dialysates and apherisates are formulated solely to achieve optimal extraction of the analytes or solutes targeted for extraction. Accordingly, for the device of invention, formulating fluids from the standpoint of returning blood, blood cells, or plasma into the bloodstream is immaterial.

In a patient with a normal urinary system, the intracorporeal blood purifier performs such functions as cytapheresis or leukapheresis in myeloproliferative disease and the extraction of autoimmune antigens or debris of killed bacteria beyond the ability of innate kidneys, the diversity of targets contingent upon the availability of target-binding superparamagnetic iron oxide magnetically susceptible carrier agents or intermediary agents having an affinity for the target which has been formulated to be infused as a ferrofluid into the bloodstream.

Infusion is usually through a body surface port positioned subcutaneously in the pectoral region with central line attached to a great vessel by means of a side-entry jacket as described and shown in copending parent application Ser. No. 15/998,002 to include FIGS. 27, 28, and 45 therein, and copending application Ser. No. 16/873,914 FIGS. 26A thru 26C, 27A thru 27C, with a urinary prosthesis shown in FIGS. 28 thru 30 therein.

In a patient with a normal upper urinary tract but lacking the lower tract, function of the intracorporeal blood purifier is the same as in a patient with a completely intact urinary system, but with the lower bladder delivery portion of the mechanism shown in FIG. 2 positioned within the prosthetic neobladder or ureteral confluence chamber 145 of the urinary prosthesis described and shown in copending application Ser. No. 16/873,914. For the magnetically implemented extractate dumping feature to work, the dome, or roof, of the neobladder in such an embodiment must adjust in elevation during filling, the same applying in a patient with a continent bladder reconstruction. In the drawing figures, an innate urinary bladder is shown as 92, while a prosthetic neobladder or ureteral confluence chamber is shown as 145.

In a patient having undergone a pelvic evisceration, the intracorporeal blood purifier as the extractive, or negative component of a prosthetic disorder response system cooperates with the urinary prosthesis shown in FIGS. 28 thru 30 of copending application Ser. No 16/873,914 and the positive, or substance (pharmaceuticals, enzymes, hormones) furnishing component of the disorder response system to provide renal function, or if the patient presents with myeloproliferative or autoimmune disease, for example, assisted in addition to normal function.

Depending upon the condition of the patient, injectable or infusible body surface ports such as those shown in copending application Ser. Nos. 16/873,914 and parent application Ser. No. 15/998,002, can be positioned elsewhere such as in the pectoral region. So that FIG. 1 can represent the use of permanent magnets as well as electromagnets, or magnets of either kind in succession, electrical wires have been omitted. In the rear view of FIG. 1, the dialysate, apherisate, or water flush line 79 is shown running contiguously in parallel to the left-hand side of the inferior vena cava IVC.

Accordingly, peristaltic pump 56 recirculates the dialysate or other fluid through the flush-line which passes successive magnet poles 75 and extraction and transit windows 81, the implanted microprocessor effecting the washing away of any debris adherent to poles 75 at intervals and if appropriate to the specific function performed, by stopping the pulsing action if used of magnets 74 if electromagnets, accelerating pump 56 according to a flush timing cycle. Any residual debris observed sonographically at an occasional visit to the clinic to check the operation of the system is dissolved with a solvent introduced through port 16 in FIG. 2.

FIG. 2 shows a more detailed view of the inferior, or caudal, end of the circuit where the magnetically separated target analyte is delivered into the urinary bladder for normal elimination in the urine. Peristaltic pump-driven dialysate, apherisate, or water flush-line 79 circulates the fluid around the circuit, until as shown in FIGS. 1 and 2, it is removed and replenished through the access lines connected to the body surface port positioned to the right-hand side of the mons pubis. Flush-line 79 is simultaneously emptied and replenished with fresh dialysate or apheresis fluid through fluid exchange lines 97 and 99.

The lower portion of FIG. 1 provides an overall schematic, or nonanatomical, view and FIG. 2 a more detailed view of the connection between the magnetic separation circuit and urinary bladder 92, into which the debris is discarded for expulsion in the urine, accomplished by reversing the extraction relation so that debris which had been drawn into flush-line 79 by chain jackets 91 is now drawn into bladder 92 by magnet jacket 93 positioned near to the bladder neck on the inferolateral surface of bladder 92.

Bladder 92 is to be taken as partially filled, semiflaccid or collapsed state before filling causes the bladder roof to be adjusted in elevation. Continued filling of bladder 92 progressively reduces the distance between diffusion membrane or cytapheresis slit-valve extraction window 94 in the side of flush-line 79 and a ringed, or framed, about window of complementary shape in bladder 92. This mechanism is also described in copending parent application Ser. No. 15/998,002.

Continued expansion upward of bladder 92 therefore compresses pliant accordion tubing 95 connected to the edges of the two windows as a surround thus damming them about throughout the distance traveled, that is the excursion or throw, from maximum separation with bladder 92 empty to flush apposite relation with bladder 92 full. Depending upon the amount of debris, magnet 93 is used in either of two ways. If the debris is sparse, then patients with a normal urinary system seldom if ever voiding the moment urge sensation is felt, contact between flush-line and bladder transit window ring or frame surrounds persists and sends a signal to the implant microprocessor to energize magnet 93 over a few cycles, or circuits of the flush fluid through flush-line 79.

The replacement of the fluid in the flush-line is addressed above in the section entitled Background to the Invention. If the debris is considerable, then the implant microprocessor energizes the solvent reservoir outlet pump to release solvent through the accessory channel 11 of each magnet 74 to assist flush-line 79 in washing away any accumulation of debris, and magnet 93 is periodically energized over a longer interval for higher amplitude field strength pulsing to pull the debris through extraction window 94 and the window in bladder 92 into bladder 92 to include times when bladder 92 is not full. In FIG. 1, intracorporeal blood purifier druglines are labeled as part number 11 whereas those elsewhere, such as in the urinary prosthesis shown in FIG. 4 are labeled part number 8.

When the patient has been cystectomized, the same arrangement is applied to neoureters 144 and 144' confluence chamber 145 in FIG. 4. As shown in FIG. 43 of parent application Ser. No. 15/998,002, bending of strain gauge 107 in neourethral 105 confluence chamber 102 causes impeller 106 to empty chamber 102 through one-way elastic slit-valve 108 into collection bag 101 automatically. Patients who have had their entire urinary tract removed due to malignancy leaving them fully dependent upon dialysis pending a kidney transplant use a comparable system wherein the blood purification device is positioned as shown here within the neobladder or ureteral 144 and 144' confluence chamber 145 devised to adjust in shape during filling as would a normal innate bladder.

Alternatively, Patients who have had their entire urinary system removed due to malignancy leaving them fully dependent upon dialysis pending a kidney transplant use a comparable system wherein the debris is drawn into a chamber flushed clean when the fluid is replaced. For this purpose, a separate extracorporeal component shown in FIG. 3 with dialysate or apheresis fluid reservoir and actuating pump 119 shown as peristaltic, or roller, in type, and similar to that shown toward the top of FIG. 1 to circulate the dialysate 56 is used.

In a patient requiring dialysis due to impaired kidney function but not missing any part of the urinary system, ambulatory magnetic separation dialysis is as shown in FIG. 2 where the extracted debris is drawn into the urinary bladder for expulsion, the device shown in FIG. 3 used to replenish the dialysate when the need therefor is indicated by the small turbidimetric sensor-driven lamp 120 on port 16.

In FIG. 1, the choice of a peristaltic, pump 56 is to take advantage of the pulsatile, or punctuated, flow of the output, which incremental, hence, resumed with quickly recurring onset transients, allows more effective magnetic extraction of the superparamagnetic carrier-bound microparticles or nanoparticles. A pelvically eviscerated, or enterectomized, patient without ureters of a bladder requires a hybrid system such as that shown in FIGS. 1 thru 3 combined with that shown in FIG. 4 which in itself depicts a system for placement in a patient without the need for blood purification.

In the absence of a bladder, the extraction of debris from dialysate, apherisate, and water flush line 79 is into neoureteral confluence collection chamber, or neobladder 145 by the same method as is shown for a patient with a bladder in FIG. 2. Expulsion is through port 16 and into collection bag 101. As with a patient having a complete urinary system, the device shown in FIG. 3 is used to replenish spent fluid when a small turbidimetric sensor indicator lamp 120 on port 16 comes on.

As addressed shortly below, for use with patients whose entire urinary tract has been or is likely to be bilaterally removed, leaving them wholly dependent upon dialysis, nothing seen in FIG. 4 which assumes retained kidneys and ureters applies. Rather, the expulsion of extracted target analyte debris is not by extraction into urine but directly from the flush-line 79. In this case, what excess fluid should not be excessive and can be eliminated through peritoneal dialysis much less frequently than would otherwise be several times daily.

The intracorporeal blood purification mechanism having removed waste products, unneeded salt, and potassium, the small amount or excess water can be eliminated through the relatively infrequent use of peritoneal dialysis. Placement of the bladder delivery portion of the mechanism shown in FIG. 2 within the prosthetic neobladder or ureteral confluence chamber 145 allows the implanted blood purifier to be used as a renal assist device. Should the turbidimetric sensor-driven lamp 120 on port 16 come on to signal the need for fluid replacement, the patient either carries the exchange mechanism shown in FIG. 3 in a carrying pack which can also contain an inverter if electromagnets are used.

Referring now to FIG. 2, filling of the bladder gradually alters the length of a Dacron® squeezebox, or accordion-type folding tube, bringing a flush-line-to-bladder crossover window set in the lower loop of the flush-line into flush contact with the slit-valve or semipermeable membrane likewise set in a ring-surround window in the superior surface of the bladder. The Dacron® tube supports the slit-valve or semipermeable membrane in preventing urine from leaking.

A powerful magnet enclosed within a biocompatible housing having smooth edges and rounded corners positioned down on the inferolateral surface of the bladder close to the neck, hence, effectively beneath the bladder on the right-hand side of the patient (and right-hand side in the posterior views in FIGS. 1 and 2) draws the magnetically susceptible micro or nanoparticle-bound analytes targeted for extraction through the extraction window interface at 94 and into the bladder, the target analyte then expelled in the normal course of voiding urine.

Referring to FIGS. 1 and 4, when the patient has or requires a radical cystectomy as well as dialysis, the window semipermeable membrane surround in flush-line 79 is permanently bonded to the corresponding window surround in neoureteral 144 confluence chamber 145 (see, for example, Wang, Y., Jin, B., and Yao, X. 2016. "Metachronous Urothelial Carcinoma of Whole Urinary Tract in a Dialysis-dependent Patient: A Case Report," *Oncology Letters* 11(6):4027-4029; Tseng, S. F., Chuang, Y. C., and Yang, W. C. 2011. "Long-term Outcome of Radical Cystectomy in ESDR [end-stage renal disease] Patients with Bladder Urothelial Carcinoma," *International Urology and Nephrology* 43(4):1067-1071).

Not shown in FIG. 1, which depicts an intracorporeal dialysis or apheresis system in a kidney impaired patient who produces urine which is collected in native bladder 92, had it been needed in a patient having undergone pelvic evisceration to eradicate cancer, for example, a prosthetic accumulation chamber, or neobladder, shown as part number 145 in FIG. 4 would be positioned in place of a native bladder. Neobladder 145 is made of a material that adjusts in shape while filling as would a native blader.

In FIG. 4, the arrangement with a neobladder 145 then emulates that of the device with a native bladder 92 shown in FIGS. 1 and 2 in that continued filling of the neobladder progressively reduces the distance between diffusion membrane or cytapheresis resilient one-way slit-valve as extraction window 94 in the side of dialysate, apherisate, and flush-line 79 and a ringed, or framed about extraction window of complementary shape at the anterolateral surface on the roof of neobladder 145. When these come into contact subcystic magnet 93 draws the debris collected in extraction line 79 into neobladder 145.

It is normal for the native bladder 92 to change to a more spherical shape with age. Whether due to age or to surgery, if the native bladder does not rise sufficiently upon filling so that extraction line 79 and bladder 92 are brought into contact, then it is sutured side to side to constrain its adjustment in shape during filling such that the dome rises. The same manner of shape constraint upon filling applies to a native bladder 92 or a prosthetic neobladder 145. The extent to which the bladder must be filled before the disposal of extracted debris into it will proceed automatically can be adjusted through the calculated placement of the shape constraining suture and if necessary, a probe extension of subcystic magnet 93 which must not come into contact with the bladder roof.

The need for a prosthetic bladder denoting the lack of urge sensation, as described and illustrated in the copending application Ser. No. 16/873, turbine executed emptying of the bladder shown in FIG. 4 responds to a signal sent to the controller by a strain gauge. Patients in whom a continent neobladder cannot be constructed using autologous tissue, can also use the arrangement shown in FIG. 4. Expulsion of any residual debris from line 79 is by the flush fluid as it is expelled when replaced.

Less refined, or less highly defined, extraction of different type analytes simultaneously is through a one-way abaxially opening slit-valve. Since to replace the membrane leading into the fluid circuit would require reentry to replace the mechanism, if there is a question as to the prospective need for more than one kind of analyte, the slit is used. If greater selectivity is required, the type membrane or slit-valve can be alternated from one magnet to the next, the number thereof greater than shown in FIG. 1 where only one side of the circuit carries magnets and the size of these are shown somewhat larger than the actual.

While successive extraction and transit windows 81 moving along the extraction circuit can be chosen for different target analytes, a given patient is more likely to need one type so that extraction and transit windows 81 can all incorporate bundled semipermeable fibers for dialysis, or a one-way abaxially opening slit-valve for cytapheresis at the extraction transit window, which out of view, is unshown in the frontal view of FIG. 1. The thickness and resilience of the slit-valve or porousness of the semipermeable membrane is selected to match the extractive field strength—or with an electromagnet the range of variability in the extractive field strength.

The debris is thus flushed out with the spent dialysate through intracorporeal outflow line 97, the outflow opening in port 16, and the chamber extracorporeal outflow line 121 for deposition as 98 in chamber at the same time that fresh dialysate 101 (or apheresis fluid) is pumped through chamber outflow line 122, port 16 inflow opening, and intracorporeal inflow line 99 through coupling 100 into flush-line 79. In this manner, spent dialysate or apheresis fluid is used to flush out toxic debris in lieu of urine. Part number 120 on body surface port 16 is a turbidimetry indicator lamp which indicates the need to replenish the dialysate or apherisate once reduced in light transmissivity due to the degree of the extractate load.

Power-conserving measures such as pulsed traction, energy optimized electromagnets, and silicon-iron crystal bonded to the analyte or analytes to be extracted, or extractate, notwithstanding, the completely ambulatory system still requires more frequent recharging of button cells in port 16, a small implanted battery pack, or direct connection to an electrical outlet. Recharging in any stationary location is facilitated with the aid of transdermal energy transfer. Clearly, even if the system were not adequate to avoid the clinic entirely, the patient is still spared the onerous imposition of visiting so frequently or spending as much time connected to an extracorporeal apheresis or dialysis machine.

Power Source

In a fully implanted embodiment which includes electromagnets, these should be used sparingly, with an object of approximating the freedom of movement during blood purification by normal kidneys and liver without the tethering posed by a power cord or the impediment of having to wear a power and inverter pack. Energy is most conveniently accomplished through the use of a body surface port with small power supply and rechargeable battery or higher capacity stacked rechargeable button cells to allow power replenishment by plugging into an ordinary outlet. That this allows recharging anywhere is a distinct benefit and safety factor.

When the patient wishes to avoid the need for a body surface port despite its multiple uses, recharging of an implanted battery, which may consist of higher capacity stacked rechargeable button cells, is by transdermal or transcutaneous energy transfer, addressed in the copending parent application hereto, Ser. No 15/998,002; U.S. Pat. Nos. 11,013,858; and 11,389,171.

With a home and workplace equipped with energy transmission apparatus to recharge implanted batteries through an energy transmission antenna, the patient is spared the need to periodically plug a power supply into a receptacle while at home or work. The obvious solution for the patient who is out and about is a recharging system that uses both power cord and transcutaneous energy transfer. Referring to FIG. 1, the volume of debris accumulated before flushing becomes necessary depends upon the magnetic tractive force and the quantity of the target, hence, the rate at which the residue is accumulated, and the flow frequency and rate of distilled water flush through flush-line 79.

The frequency of flushing will vary with the volume of the specific extractate, which unseen by the patient, is entered into the prescription-program for automatic execution. With peristaltic pump 56 temporarily off, the volume of debris accumulated before flushing becomes necessary depends upon the magnetic tractive force, the rate at which the residue is accumulated, and the flow rate through flush-line 79 upon recovery of pump 56.

FIG. 1 shows magnetic separation chain jackets 91 along continuous loop circuit flush-line 79 containing dialysate for intracorporeal hemodialysis, or normal saline, plasma, or water for intracorporeal cytapheresis applied to a substrate vein, shown here as the inferior vena cava, in a patient with surgically intact urinary system. As indicated, for dialysis, part number 81 in the extraction and transit windows are semipermeable diffusion-type membrane or assemblage of semipermeable fibers, while for apheresis, part number 81 is a one-way resilient slit-valve. A basic ductus side-entry jacket with mainline 13 and sideline, or sideline, 11 connected to a port at the body surface for the delivery of medicinals directly into the inferior vena cava is positioned above the level of the drawing.

With magnetic dialysis, transit past diffusion-type semipermeable membranes is not diffusion-dependent but forcible responsive to the force exerted by a magnetic field. Thus, the side-entry jacket positioned above (craniad, superior to) the extraction circuit is available to deliver agents into the substrate ductus, here the inferior vena cava, and the accessory channel 11 of each magnetic separation or extraction jacket can deliver an agent, typically a debris solvent or cleaning agent, at the magnetic poles 75. As with all ductus side-entry jackets, jackets in a chain each retain the water jacket accessory channel, drugline, or sideline 11 used to connect these to the substrate ductus with minimal if any leakage.

In most instances, however, the jacket with main and one or more sidelines craniad to the chain is sufficient for the delivery of drugs and other agents into the vein, and the lead jacket, or that superior to the others, is also available for this purpose. In a chain-jacket, accessory channels 11 are more often used to deliver a solvent where the extract resists being washed away from the magnet pole 75 by flush-line 79. While the terms sideline, drugline, accessory channel, and water jacket entry line refer to the same passageway when used to convey a drug, an adjuvant substance, or water respectively, the terms accessory channel and water jacket entry line refer to the same passageway once it has entered into the side-entry device.

Accordingly, part number 11 in FIG. 1 may be referred to as a drugline, or sideline, in relation to the mainline which usually conveys blood or urine rather than a drug and outlets through the jacket side-stem, or side-stem outlet channel through which blood or urine is diverted, or the accessory channel More specifically, however, the drug or sideline is a catheter that carries medication or a solution, for example, from a reservoir positioned subcutaneously in the pectoral region into the side-entry jacket, side-entry connector, or vascular valve, while the accessory channel is the passageway local to the end effector device which leads into it, which two are continuous.

Peristaltic pump 56 recirculates the dialysate or other fluid past through the flush-line which passes between successive magnet poles 75 and extraction and transit windows 81, the implanted microprocessor effecting the washing away of any debris adherent to poles 75 at intervals by stopping the pulsing action of magnets 74 and accelerating pump 56 according to a flush timing cycle. Any residual debris observed sonographically at an occasional visit to the clinic to check the operation of the system is dissolved with a solvent introduced through port 16 to access the magnets through accessory channel 11.

FIG. 2 provides a detailed view of the connection between the magnetic separation circuit and the native bladder 92, into which the debris is discarded for expulsion in the urine, accomplished by reversing the extraction relation so that debris which had been drawn into flush-line 79 by chain jackets 91 is now drawn into native bladder 92 by electromagnet jacket 93 positioned near to the bladder neck 94 on the inferolateral surface of native bladder 92. Native bladder 92 is shown in a partially filled, semi flaccid or collapsed state. Continued filling of native bladder 92 progressively reduces the distance between diffusion membrane or cytapheresis slit-valve extraction window 94 in the side of flush-line 79 and a ringed, or framed, about window of complementary shape in native bladder 92.

Continued expansion upward of native bladder 92 therefore compresses pliant accordion tubing 95 connected to the edges of the two windows as a surround thus damming them about throughout the distance traveled, that is the excursion or throw, from maximum separation with native bladder 92 empty to flush apposite relation with native bladder 92 full. Depending upon the amount of debris, magnet 93 is used in either of two ways. If the debris is sparse, then patients with a normal urinary system seldom if ever voiding the moment urge sensation is felt, contact between flush-line and bladder transit window ring or frame surrounds persists and sends a signal to the implant microprocessor to energize magnet 93 over a few cycles, or circuits of the flush fluid through flush-line 79.

The replacement of the fluid in the flush-line is addressed above in the section entitled Background to the Invention. If the debris is considerable, then the implant microprocessor energizes the solvent reservoir outlet pump to release solvent through the accessory channel 11 of each magnet 74 to assist flush-line 79 in washing away any accumulation of debris, and magnet 93 is periodically energized over a longer interval for higher amplitude field strength pulsing to pull the debris through extraction window 94 and the window in native bladder 92 into native bladder 92 to include times when native bladder 92 is not full.

In FIGS. 40 and 43 of parent application Ser. No. 15/998,002, when the patient has been cystectomized, the same arrangement is applied to neoureteral 105 confluence chamber 102, shown in this application as part numbers 144 and 145 respectively.

Also shown in FIG. 43 of the parent application Ser. No. 15/998,002, bending of strain gauge 107 in neoureteral 105 confluence chamber 102 causes impeller 106 to empty chamber 102 through one-way elastic slit-valve 108 into collection bag 101 automatically. Patients who have had their entire urinary system removed due to malignancy leaving them fully dependent upon dialysis pending a kidney transplant use a comparable system wherein the debris is drawn into a chamber flushed clean when the fluid is replaced.

Extraction Window Plug Removal and Placement of the Magnet Jacket

There is no method for removing a plug from the side of an unclamped blood vessel with zero blood loss. A method that comes close is the use of a foot pedal-activated small-head high speed electrical light emitting diode-lit multiport water-cooled dental handpiece to turn a miniature version of a hand drill turned hole saw without an arbor, or central pilot drill bit. Made of polyethylene terephthalate or another strong high clarity transparent polymer, the miniature shallow cup hole saw is short in aspect, or diameter to depth ratio, and has a razor-sharp saw-toothed cutting edge.

A pinhole at the side journals a needle with a wide push pin or push/pull shaped head, and arrow head-configured tip, so that the needle can be inserted up to and retracted from the opposing wall of the shallow hole saw cup. This allows the operator who can see through the transparent hole saw to angle the dental handpiece to sever a dangling plug, and the needle allows the plug to be transpierced, or skewered. These two capabilities eliminate any plug that would 'hang" along an edge to resist its removal so that the skewered plug is surely and easily extracted when the handpiece is withdrawn.

The operator uses a dab of high viscosity, high tack, high dissolution-rate molasses incapable of posing a risk of embolization on the thumb of his surgical glove to close the hole, and assisted by the pressurized streams of water from the dental handpiece and the physical barrier posed by the shallow roof of the hole saw, stops any bleeding long enough to position the magnet jacket in place and lock it the instant he withdraws his hand. All side-entry and magnet-jackets, to include those shown in FIG. 1 at the unseen under- and topsides, comprise two half cylinders joined along a spring-loaded hinge along one side and a miniature briefcase or purse-type lock at the opposite side that automatically locks the jacket shut when closed and releases by pushing down or sliding a spring-loaded clasp release button.

Accordingly, magnet jackets such as shown in FIG. 1 are fastened to the inferior vena cava by:

1. Using a dental handpiece with hole saw to cut out a plug from the side of the substrate vessel.
2. Should it adhere, or 'hang,' along an edge, skewering the plug with the push pin head-configured transpiercing needle situated toward the leading razor-sharp serrated or saw-toothed edge of the hole saw.
3. Positioning the thumb with the temporary hole sealant next to the hole or ostium just cut.
4. Instantly moving the thumb over the hole to fill it with the temporary sealant.
5. Positioning the opened magnet jacket around the inferior vena cava at the level desired.
6. Closing the magnet jacket around the inferior vena cava and snapping it shut.
7. Connecting the accessory channel (sideline, drugline) part number 11 in FIG. 1 and if an electromagnet, its electric power wire to the magnet-jacket.

The invention claimed is:

1. An intracorporeal blood purifier for implantation configured to compensate for an inadequacy in renal function due to any disease and supplement normal renal function in the treatment of a myeloproliferative disease, said blood purifier comprising a succession of disease-related analyte separation magnets configured to be placed along and in perivascular relation to a substrate vessel, wherein the separation magnets are configured to extract and deliver said disease-related analytes into the urinary bladder, said disease-related analytes having been rendered magnetically susceptible by bonding to superparamagnetic carriers, wherein said blood purifier further comprises extractive windows configured to separate the blood flowing through the substrate vessel and the extraction magnets, said extractive windows including semipermeable membranes and resilient one-way slit valves.

2. The intracorporeal blood purifier according to claim 1 wherein said blood purifier is configured to be applied to the inferior vena cava.

3. The intracorporeal blood purifier according to claim 1 wherein said blood purifier is configured to be applied to the hepatic portal vein.

4. The intracorporeal blood purifier according to claim 1 wherein said blood purifier is configured to be applied to the abdominal aorta.

5. The intracorporeal blood purifier according to claim 1 wherein said blood purifier further comprises extractive magnets of different types and field strengths to include permanent and electromagnetic magnets, wherein the electromagnets are selectively energized.

6. The intracorporeal blood purifier according to claim 1 further comprising batteries, wherein said batteries are rechargeable through a power supply plugged into an electrical outlet and by transcutaneous energy transfer through an implanted antenna.

7. The intracorporeal blood purifier according to claim 1 where the analyte to be extracted from the bloodstream is a microbial pathogen, a toxin resulting from hepatic dysfunction, an antigen the product of autoimmune disease, or a material overproduction of any type of blood cell due to a myeloproliferative disease.

8. The intracorporeal blood purifier according to claim 1, wherein said blood purifier is configured to extract different types of disease-related analytes from the bloodstream simultaneously.

9. The intracorporeal blood purifier according to claim 1 where the superparamagnetic carriers are configured to impart magnetic susceptibility and are bound to the disease-related analyte regardless of whether this bonding is due to an inherent affinity for the analyte or due to having been bonded to an intermediary substance with an inherent affinity for the disease-related analyte.

10. The intracorporeal blood purifier according to claim 1 wherein said blood purifier continuously or intermittently without generating an experiential correlate of internal movement.

11. An implanted automatic prosthetic disorder response system comprising:

an extractive, or negative component, wherein the extractive component is an intracorporeal blood purifier configured for implantation in the abdominopelvic and abdominal regions and configured to compensate for an inadequacy in renal function due to any disease and supplement normal renal function in the treatment of a myeloproliferative disease, said blood purifier comprising a succession of disease-related analyte separation magnets along and in perivascular relation to a substrate vessel, wherein the separation magnets are configured to extract and deliver said disease-related analytes into the urinary bladder, said disease-related analytes having been rendered magnetically susceptible by bonding to superparamagnetic carriers; and a positive component, wherein the positive component cooperates with the negative component by detecting the need for and directly targeting essential and curative substances to the sites of disease in immediate cooperation with the extractive component which is configured to extract different type disease-related analytes such as pathogenic, autoimmune, and supernumerary, from the bloodstream simultaneously; wherein said blood purifier further comprises extractive windows configured to separate the blood flowing through the substrate vessel and the extraction magnets, said extractive windows including semipermeable membranes and resilient one-way slit-valves.

12. The implanted automatic prosthetic disorder response system of claim 11, wherein said blood purifier functions continuously or intermittently without generating an experiential correlate of internal movement.

* * * * *